United States Patent [19]

Findeisen et al.

[11] 4,360,479
[45] Nov. 23, 1982

[54] PROCESS FOR THE PREPARATION OF ACYL CYANIDE COMPOUNDS

[75] Inventors: Kurt Findeisen, Odenthal; Hans Krätzer, Wuppertal; Manfred Lenthe, Odenthal, all of Fed. Rep. of Germany

[73] Assignee: Bayer Aktiengesellschaft, Leverkusen, Fed. Rep. of Germany

[21] Appl. No.: 276,774

[22] Filed: Jun. 24, 1981

[30] Foreign Application Priority Data

Jul. 4, 1980 [DE] Fed. Rep. of Germany ....... 3025304

[51] Int. Cl.$^3$ .................... C07C 51/08; C07C 51/083
[52] U.S. Cl. ................ 260/545 R; 544/163; 548/128; 548/236; 548/248; 548/265; 548/268; 548/261; 548/330; 548/342; 548/378; 548/540; 546/189; 549/491
[58] Field of Search ..................................... 260/545 R

[56] References Cited

U.S. PATENT DOCUMENTS

| | | | |
|---|---|---|---|
| 2,806,634 | 8/1979 | Bosse et al. | 260/545 R |
| 4,117,008 | 9/1978 | Kleuk et al. | 260/545 R |

FOREIGN PATENT DOCUMENTS

| | | | |
|---|---|---|---|
| 5484 | 5/1979 | European Pat. Off. | |
| 1813184 | 8/1969 | Fed. Rep. of Germany | 260/545 R |
| 2614240 | 10/1977 | Fed. Rep. of Germany | |
| 2614241 | 10/1977 | Fed. Rep. of Germany | |
| 56-29526 | 3/1981 | Japan | 260/545 R |
| 583646 | 12/1946 | United Kingdom | |

OTHER PUBLICATIONS

Oku et al., Bull. Chem. Soc. Jap., vol. 52, (10), 1979, pp. 2966–2969.

*Primary Examiner*—Delbert R. Phillips
*Assistant Examiner*—Frederick W. Pepper
*Attorney, Agent, or Firm*—Felfe & Lynch

[57] ABSTRACT

This invention relates to a new process for the preparation of acyl cyanides of the general formula $$R^1\text{—CO—CN} \qquad (I)$$

wherein $R^1$ is an optionally substituted alkyl radical up to 18 carbon atoms, an optionally substituted cycloalkyl radical with 3 to 12 carbon atoms, an optionally substituted aryl radical or an optionally substituted 5- or 6-membered heterocyclic radical, which can additionally also be fused with a benzene ring, which process comprises reacting a carboxylic acid anhydride of the formula $$R^1\text{—CO—O—CO—}R^1 \qquad (II)$$

with an alpha-hydroxynitrile of the formula $$\begin{array}{c} R^2 \quad OH \\ \diagdown \, \diagup \\ C \\ \diagup \, \diagdown \\ R^3 \quad CN \end{array} \qquad (III)$$

in which $R^2$ and $R^3$ are identical or different and represent a hydrogen atom, an optionally substituted alkyl radical with 1 to 18 carbon atoms, an optionally substituted cycloalkyl radical with 3 to 12 carbon atoms, an optionally substituted aryl radical or an optionally substituted 5- or 6-membered heterocyclic radical, which can additionally also be fused with a benzene ring. The acyl cyanides (I) are known compounds and can be used as starting material for the synthesis of herbicides.

22 Claims, No Drawings

PROCESS FOR THE PREPARATION OF ACYL CYANIDE COMPOUNDS

This invention relates to a new process for the preparation of certain acyl cyanides by reacting carboxylic acid anhydrides with alpha-hydroxynitriles. The acyl cyanides produced are known compounds and can be used as starting materials for the synthesis of herbicides.

It is known that carboxylic acid anhydrides can be reacted with hydrocyanic acid at high temperatures in the gas phase in the presence of certain catalysts to give acyl cyanides (see British Pat. No. 583,646). The main disadvantage of this process is that the yields which it gives are too low; it is therefore of no interest as an industrial process.

It is also known that acyl cyanides can be obtained by reacting carboxylic acid anhydrides with alkali metal cyanides or liquid anhydrous hydrocyanic acid, if appropriate in the presence of a diluent, at temperatures between 50° and 250° C. and removing the resulting acyl cyanides from the reaction medium by distillation immediately after then have been formed (see DE-OS (German Published Specification) No. 2,614,241), or by reacting carboxylic acid anhydrides with an alkali metal cyanide or liquid anhydrous hydrocyanic acid in the presence of the corresponding carboxylic acid chloride, if appropriate in the presence of a diluent, at temperatures between 50° and 300° C. (see DE-OS (German Published Specification) No. 2,614,240). Both the above-mentioned processes have the disadvantage that only moderate yields of aliphatic acyl nitriles are achieved; thus, for example, pivaloyl cyanide can be prepared in yields of 71 or 67% of theory.

The present invention now provides a process for the preparation of an acyl cyanide of the general formula $$R^1\text{—CO—CN} \tag{I}$$

in which $R^1$ represents an optionally substituted alkyl radical with up to 18 carbon atoms, an optionally substituted cycloalkyl radical with 3 to 12 carbon atoms, an optionally substituted aryl radical or an optionally substituted 5-membered or 6-membered heterocyclic radical, which can additionally also be fused with a benzene ring, in which a carboxylic acid anhydride of the general formula $$R^1\text{—CO—O—CO—}R^1 \tag{II}$$

in which $R^1$ has the above-mentioned meaning, is reacted with an α-hydroxynitrile of the general formula

(III)

in which $R^2$ and $R^3$ are identical or different and represent a hydrogen atom, an optionally substituted alkyl radical with 1 to 18 carbon atoms, an optionally substituted cycloalkyl radical with 3 to 12 carbon atoms, an optionally substituted aryl radical or an optionally substituted 5-membered or 6-membered heterocyclic radical, which can additionally also be fused with a benzene ring, optionally in the presence of a diluent, and optionally at a temperature between 250° and 600° C. The process of the present invention gives the acyl cyanides of formula (I) in high yields and in a high purity.

It is to be described as exceptionally surprising that acyl cyanides of the formula (I) are accessible in a high yield and excellent purity by the process according to the invention, since, in view of the known state of the art, it was to be expected that, as the main reaction, as illustrated by the following equations, either acylated cyanohydrins would be formed according to equation (a), or, according to equation (b), unsaturated nitriles would be formed by pyrolytic degradation of the cyanohydrins (see, for example, V. Migrdichian, "The Chemistry of Organic Cyanogen Compounds", Reinhold Publishing Corp., New York, 1947, page 190), or secondary products of these nitriles, for example polymers would be formed:

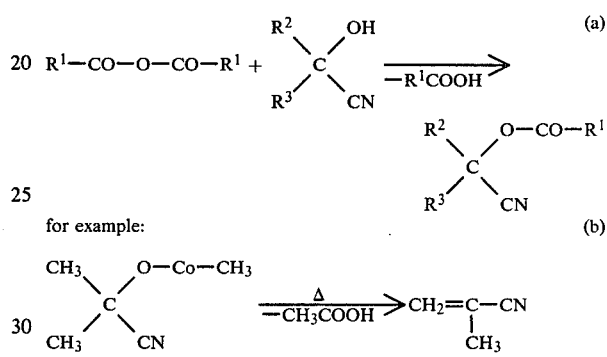

for example:

A particular advantage compared with the processes already known is that the process according to the invention also gives high yields of aliphatic acyl cyanides. An additional advantage compared with the catalytic process known from British Patent Specification No. 583,646 is that the process according to the invention requires no catalyst. It should also be emphasized that working up presents no problems in the process according to the invention: the reaction products can in general easily be separated off by distillation or filtration; the by-products of the reaction, that is to say carboxylic acids and ketones or aldehydes, can be converted back into the starting materials, that is to say carboxylic acid anhydrides or cyanohydrins, by known processes.

If pivalic anhydride and acetone cyanohydrin are used as starting substances, the course of the reaction according to the present invention is illustrated by the following equation:

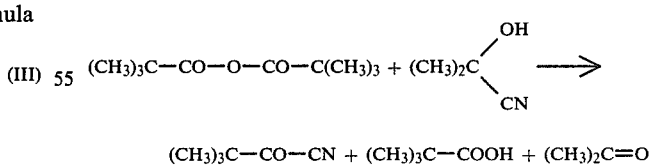

$$(CH_3)_3C\text{—CO—CN} + (CH_3)_3C\text{—COOH} + (CH_3)_2C\text{=}O$$

Preferred carboxylic acid anhydrides of formula (II) used as starting substances in the process of the present invention are those in which $R^1$ represents a straight-chain or branched alkyl radical with 1 to 4 carbon atoms, it being possible for each of these alkyl radicals to be substituted by alkoxy with 1 to 4 carbon atoms, carbalkoxy with 1 to 4 carbon atoms in the alkoxy group, nitro, nitrile and/or halogen (such as fluorine, chlorine, bromine, or iodine); represents a cycloalkyl radical which has 5 or 6 carbon atoms in the ring system and is optionally substituted by alkyl, alkoxy or carbalkoxy with in each case up to 4 carbon atoms, nitro, nitrile and/or halogen; represents an aryl radical, preferably a phenyl or naphthyl radical, which is optionally substituted by alkyl, alkoxy or carbalkoxy with in each case up to 4 carbon atoms, nitro and/or halogen (such as fluorine, chlorine, or bromine); or represents a 5-membered or 6-membered heterocyclic radicals which is optionally substituted by alkyl, alkoxy or carbalkoxy with in each case up to 4 carbon atoms, nitro, nitrile and/or halogen (such as fluorine, chlorine or bromine) and which optionally contains 1 to 3 hetero-atoms, such as oxygen, sulphur and/or nitrogen, in the ring, and is optionally fused to a benzene ring.

Examples which may be mentioned of preferred heterocyclic radicals $R^1$ are: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

The carboxylic acid anhydrides of the formula (II) are known, or then can be prepared by processes, which are in themselves known (see, for example, Houben-Weyl, Methoden der Organischen Chemie (Methods of Organic Chemistry), 4th Edition, Volume VIII, page 476–480 (1952)).

Preferred examples of carboxylic acid anhydrides of the formula (II) which may be mentioned specifically are: acetic anhydride, propionic anhydride, pivalic anhydride, cyclohexanecarboxylic acid anhydride, benzoic anhydride, m-chlorobenzoic anhydride, 3,5-dichlorobenzoic anhydride, naphthalene-1-carboxylic acid anhydride and 1-phenyl-5-pyrazolone-3-carboxylic acid anhydride. Anhydrides which may be mentioned as particularly preferred are pivalic anhydride and the aromatic carboxylic acid anhydrides, and from this group, in particular, benzoic anhydride.

Preferred α-hydroxynitriles of formula (II) used as starting substances in the process of the present invention are those in which $R^2$ and $R^3$ represent identical or different radicals, preferably a straight-chain or branched alkyl radical with 1 to 8 carbon atoms, a cycloalkyl which has 5 or 6 ring carbon atoms and is optionally substituted by alkyl or carbalkoxy with in each case 1 to 5 carbon atoms, or a phenyl or naphthyl radical, optionally substituted by alkyl, halogenoalkyl, alkoxy or carbalkoxy with in each case up to 4 carbon atoms, nitro and/or halogen (such as fluorine, chlorine or bromine).

The α-hydroxynitriles (cyanohydrins) of the formula (III) are known, or they can be prepared by processes which are in themselves known (see, for example, Houben-Weyl, *Methoden der organischen Chemie* ("Methods of Organic Chemistry"), 4th Edition, Volume VIII, pages 274–277 (1952)).

As preferred examples of α-hydroxynitriles of the formula (III) there may be mentioned: acetone cyanohydrin, methyl ethyl ketone cyanohydrin and cyclohexanone cyanohydrin.

Possible diluents which can be employed in carrying out the process according to the invention are any of the inert organic solvents which do not undergo a chemical reaction either with the carboxylic acid anhydrides or with the α-hydroxycarboxylic acid nitriles (cyanohydrins). Such solvents are, for example, the xylenes (such as o-xylene), chlorobenzene, o-dichlorobenzene, the trichlorobenzenes, nitrobenzene, tetramethylene sulphone and carboxylic acid nitriles (such as acetonitrile or propionitrile). An excess of carboxylic acid anhydride of formula (II) or, in particular, of α-hydroxynitrile of formula (III) is also a suitable diluent. In principle, however, it is also possible to carry out the reaction according to the invention without a diluent.

The reaction temperature can be varied within a relatively wide range. In general, the reaction is carried out at a temperature between 250° and 600° C., preferably between 300° and 500° C.

The reaction is in general carried out under normal pressure.

In carrying out the process according to the invention 0.7 to 5 moles, preferably 1 to 4 moles, of α-hydroxynitrile of formula (III) are in general employed per mole of carboxylic acid anhydride of formula (II).

When the reaction had ended, the products are usually worked up and isolated by distillation and, if appropriate, recrystallization.

In a particular process variant, the reaction according to the invention can also be carried out continuously.

The acyl cyanides of the formula (I) which can be prepared by the process according to the invention are widely known (see, for example, Thesing et al., Angew. Chem. 68, 425–435 (1956), and furthermore DE-OS'en (German Published Specifications) Nos. 2,528,211; 2,614,240; 2,614,241; 2,614,242; 2,624,891; 2,642,140; 2,642,199; 2,708,182; 2,708,183; 2,717,075 and 2,820,575); they are valuable starting substances, for example for the synthesis of 1,2,4-triazan-5-ones, which have outstanding herbicidal properties (see, for example, DE-OS (German Published Specification) No. 2,224,161; and German Patent Specification No. 1,795,784).

Thus, for example, 3-methyl-4-amino-6-phenyl-1,2,4-triazin-5(4H)-one of the formula

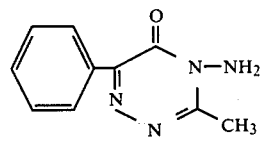

can be prepared by a procedure in which, in a first stage, benzoyl cyanide is reacted with ethanol in the presence of concentrated hydrochloric acid, and the phenylglyoxylic acid ethyl ester thereby formed is reacted, in a second stage, with acetylhydrazine, whereupon 1-phenylglyoxylic acid ethyl ester-2-acetylhydrazone is formed, and is then converted, in a third stage, into the above-mentioned end produce with hydrazine hydrate in the presence of pyridine.

This multi-stage synthesis can be represented by the following equations:

1st stage:

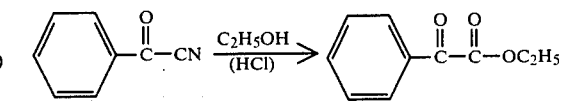

2nd stage:

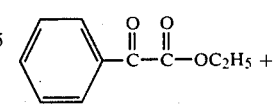

-continued

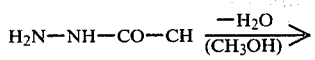

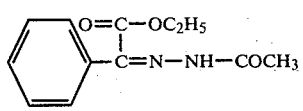

3rd stage:

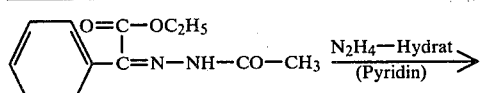

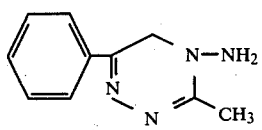

The pivaloyl cyanide which can be prepared according to the invention can be converted, for example, into the herbicidal active compound 3-methylthio-4-amino-6-tert.-butyl-1,2,4-triazin-5-(4H)-one by known processes (see DE-OS (German Published Specification) No. 2,733,180, U.S. Patent Specification No. 4,175,188 and also German Patent Applications P Nos. 30 02 203.8. P 30 03 541.7 and P 30 09 043.8).

The process according to the invention is illustrated by the following preparative Examples:

PREPARATIVE EXAMPLES

EXAMPLE 1

(CH₃)₃C—CO—CN 186 g (1 mole) of pivalic anhydride and 255 g (3 moles) of acetone cyanohydrin were mixed and the mixture was passed dropwise, in the course of three hours, through a glass tube which was packed with Raschig rings and heated to 450° C. The reaction products were collected in a cooled receiver and then subjected to fractional distillation. Yield: 97.7 g of pivaloyl cyanide (88% of theory); boiling point: 124°–126° C.

The excess acetone cyanohydrin and the unreacted pivalic anhydride were used for the next batch.

EXAMPLE 2

113 g (0.5 mole) of benzoic anhydride and 127.5 g (1.5 moles) of acetone cyanohydrin were passed dropwise, in the course of one hour, through a 90 cm long Duran glass tube (diameter: 3.8 cm) which was heated to 400° C. and packed with Raschig rings. The resulting reaction mixture was then boiled up with wash benzine; after cooling, the benzoic acid which has precipitated was filtered off. The filtrate was first concentrated by stripping off the highly volatile constituents, and was then subjected to fractional distillation.

Yield: 49.1 g of benzoyl cyanide (75% of theory); melting point: 32° C.

It will be understood that the specification and examples are illustrative but not limitative of the present invention and that other embodiments within the spirit and scope of the invention will suggest themselves to those skilled in the art.

What is claimed is:

1. Process for the preparation of an acyl cyanide compound of the formula $$R^1—CO—CN \qquad (I)$$

wherein $R^1$ is an optionally substituted alkyl radical up to 18 carbon atoms, an optionally substituted cycloalkyl radical with 3 to 12 carbon atoms, an optionally substituted aryl radical or an optionally substituted 5- or 6-membered heterocyclic radical, which can additionally also be fused with a benzene ring, which process comprises reacting a carboxylic acid anhydride of the formula $$R^1—CO—O—CO—R^1 \qquad (II)$$

with an alpha-hydroxynitrile of the formula

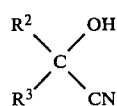

(III)

in which $R^2$ and $R^3$ are identical or different and represent a hydrogen atom, an optionally substituted alkyl radical with 1 to 18 carbon atoms, an optionally substituted cycloalkyl radical with 3 to 12 carbon atoms, an optionally substituted aryl radical or an optionally substituted 5- or 6-membered heterocyclic radical, which can additionally also be fused with a benzene ring.

2. Process as claimed in claim 1 wherein $R^1$ is optionally substituted alkyl of up to 18 carbon atoms.

3. Process as claimed in claim 1 wherein $R^1$ is optionally substituted cycloalkyl of 3 to 12 carbon atoms.

4. Process as claimed in claim 1 wherein $R^1$ is an optionally substituted aryl radical.

5. Process as claimed in claim 1 wherein $R^1$ is an optionally substituted 5- or 6-membered heterocyclic radical.

6. Process as claimed in claim 5 wherein said heterocyclic radical is fused with a benzene ring.

7. Process as claimed in claim 1 wherein $R^2$ and $R^3$ are identical.

8. Process as claimed in claim 1 wherein $R^2$ and $R^3$ are different.

9. Process as claimed in claim 1 wherein the process is carried out in the presence of a diluent.

10. Process as claimed in claim 9 wherein the diluent is a xylene, chlorobenzene, o-dichlorobenzene, a trichlorobenzene, nitrobenzene, tetramethylene sulphone or a carboxylic acid nitrile.

11. Process as claimed in claim 1 wherein the reaction is carried out at a temperature between 250° and 600° C.

12. Process as claimed in claim 11 wherein the reaction is carried out at a temperature between 300° and 500° C.

13. Process as claimed in claim 1 in which a carboxylic acid anhydride of the formula $$R^1—CO—O—CO—R^1 \qquad (II)$$

wherein $R^1$ is a straight-chain or branched alkyl radical with 1 to 4 carbon atoms, each radical being substituted by alkoxy with 1 to 4 carbon atoms, carbalkoxy with 1 to 4 carbon atoms in the alkoxy group, nitro, nitrile and halogen; is a cycloalkyl radical of 5 or 6 carbon atoms in the ring system and is optionally substituted by alkyl, alkoxy or carbalkoxy with, in each case, up to 4 carbon atoms, nitro, nitrile and halogen; is an aryl radical which is optionally substituted by alkyl, alkoxy or carbalkoxy with, in each case, up to 4 carbon atoms, nitro and halogen; or is a 5- or 6-membered heterocyclic radical which is optionally substituted by alkyl, alkoxy or carbalkoxy with, in each case, up to 4 carbon atoms, nitro, nitrile and halogen and which, optionally, contains 1 to 3 hetero-atoms which are oxygen, sulphur and nitrogen in the ring and is, optionally, also fused to a benzene ring is used.

14. Process as claimed in claim 13 wherein the carboxylic acid anhydride of formula (II) is pivalic anhydride or benzoic anhydride.

15. Process as claimed in claim 1 wherein an alphahydroxynitrile of the formula

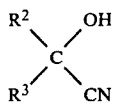

wherein $R^2$ and $R^3$ are identical or different radicals, selected from a straight-chain or branched alkyl radical with 1 to 8 carbon atoms, a cylcoalkyl which has 5 or 6 ring carbon atoms and is optionally substituted by alkyl or carbalkoxy with, in each case, 1 to 5 carbon atoms, and a phenyl or naphthyl radical, optionally substituted by alkyl, haloalkyl, alkoxy or carbalkoxy with, in each case, up to 4 carbon atoms, nitro and halogen is used.

16. Process as claimed in claim 15 wherein the alpha-hydroxynitrile of formula (III) is acetone cyanohydrin, methylethyl ketone cyanohydrin or cyclohexanone cyanohydrin.

17. Process as claimed in claim 1 wherein 0.7 to 5 moles of the alpha-hydroxynitrile of formula (III) are employed per mole of the carboxylic acid anhydride of formula (II).

18. Process as claimed in claim 17 wherein 1 to 4 moles of the alpha-hydroxynitrile of formula (III) are employed per mole of the carboxylic acid anhydride of formula (II).

19. Process as claimed in claim 1 wherein pivalic anhydride is reacted with acetone cyanohydrin to produce pivaloyl cyanide.

20. Process as claimed in claim 1 wherein benzoic anhydride is reacted with acetone cyanohydrin to produce benzoyl cyanide.

21. Process as claimed in claim 19 wherein the mole ratio of pivalic anhydride to acetone cyanohydrin is about 1:3.

22. Process as claimed in claim 20 wherein the mole ratio of pivalic anhydride to acetone cyanohydrin is about 1:3.

* * * * *